United States Patent
Dubois et al.

(10) Patent No.: US 8,816,108 B2
(45) Date of Patent: Aug. 26, 2014

(54) PROCESS FOR THE PURIFICATION OF A FATTY ACID ALKYL ESTER BY LIQUID/LIQUID EXTRACTION

(75) Inventors: Jean Luc Dubois, Millery (FR); Antoine Piccirilli, Poitiers (FR); Julien Magne, Roches-primaries-andille (FR)

(73) Assignee: Arkema France, Colombes (FR)

( * ) Notice: Subject to any disclaimer, the term of this patent is extended or adjusted under 35 U.S.C. 154(b) by 0 days.

(21) Appl. No.: 13/808,808

(22) PCT Filed: Jun. 24, 2011

(86) PCT No.: PCT/FR2011/051462
§ 371 (c)(1),
(2), (4) Date: Mar. 21, 2013

(87) PCT Pub. No.: WO2012/004489
PCT Pub. Date: Jan. 12, 2012

(65) Prior Publication Data
US 2013/0211115 A1    Aug. 15, 2013

(30) Foreign Application Priority Data
Jul. 8, 2010 (FR) .................................. 10 55555

(51) Int. Cl.
*C11B 7/00* (2006.01)
(52) U.S. Cl.
USPC ........................................ 554/210; 554/206
(58) Field of Classification Search
USPC ................................................. 554/206, 210
See application file for complete search history.

(56) References Cited

U.S. PATENT DOCUMENTS

| 7,592,470 B2 | 9/2009 | Lacome et al. |
| 2005/0266139 A1 | 12/2005 | Lacome et al. |
| 2009/0260280 A1* | 10/2009 | Klausmeier .................... 44/302 |

FOREIGN PATENT DOCUMENTS

| FR | 2 855 517 | 12/2004 |
| FR | 2855517 A1 * | 12/2004 | .............. C07C 67/03 |
| JP | 2008 156579 | 7/2008 |
| JP | 2008156576 A * | 7/2008 |

OTHER PUBLICATIONS

International Search Report for PCT/FR2011/051462, Date of the actual completion of the international search: Oct. 12, 2011, Date of mailing of the international search report: Oct. 19, 2011.
Momentive Performance Materials Japan KK, "Electroconductive silicone rubber composition," Patent Abstracts of Japan, Publication Date: Jul. 10, 2008; English Abstract of JP-2008 156579.

* cited by examiner

*Primary Examiner* — Deborah D Carr
(74) *Attorney, Agent, or Firm* — Millen, White, Zelano & Branigan, P.C.

(57) ABSTRACT

The present invention relates to a process for the selective extraction of monoglycerides present in a fraction of fatty acid alkyl esters (FAAEs), comprising at least one stage of liquid-liquid extraction by means of a polar solvent (PS) comprising a light alcohol and optionally of a nonpolar solvent (NS) comprising a solvent which is immiscible with the light alcohol.

The present invention relates in particular to a fraction of fatty acid alkyl esters (FAAEs) of vegetable or animal origin, used in particular in biodiesels, capable of being obtained according to the process of the invention, so that its content of monoglycerides is less than 0.6%.

21 Claims, 1 Drawing Sheet

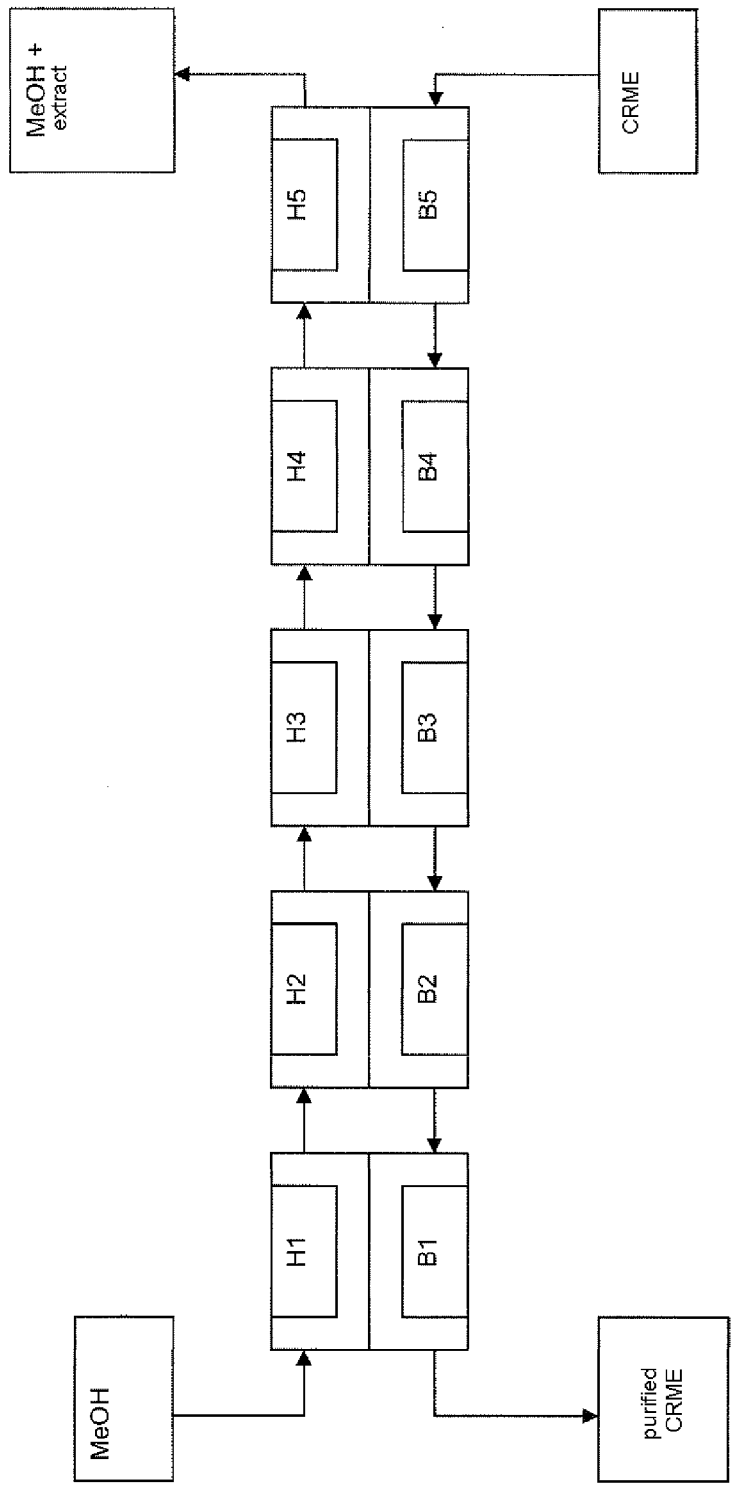

PROCESS FOR THE PURIFICATION OF A FATTY ACID ALKYL ESTER BY LIQUID/LIQUID EXTRACTION

The present invention relates to a process for the extraction of the residual monoglycerides which occur in a fraction of fatty acid alkyl esters resulting from transesterification which are used in particular to manufacture biodiesel.

The term "fatty acid alkyl esters" (abbreviation FAMEs) is understood to mean, within the meaning of the invention, preferably the esters resulting from the transesterification of $C_1$ to $C_8$ alcohols with $C_8$ to $C_{36}$ fatty acids. These FAMEs thus correspond to the formula: $R^1CO-OR^2$, where $R^1CO$ is an aliphatic acyl group comprising from 8 to 36 carbon atoms and $R^2$ is a linear or branched alkyl group comprising from 1 to 8 carbon atoms.

Thus, fatty acid methyl esters (abbreviation FAMEs) are obtained by transesterification of fatty acids of vegetable or animal origin with methanol, generally in the presence of a basic catalyst, such as NaOH. The fatty acids originate mainly from vegetable oils, such as rapeseed, sunflower, soybean, peanut, olive, sesame, safflower, coconut, palm, castor or jatropha oil, microalgae and the like. The fatty acids can also originate from animal sources, for example from waste originating from the food processing industry, such as abattoir waste, from animal fats, such as chicken, beef, pig or fish fats, or from used frying oils.

Fatty acid methyl esters (abbreviation FAMEs) are the major constituents of the biodiesel produced today. For this reason, the present invention is described generally in the continuation of the text and the examples with reference to the purification of a fraction of fatty acid methyl esters. Nevertheless, the process of the invention is obviously not limited to the purification of the fractions of fatty acid methyl esters but applies to any fraction of fatty acid alkyl esters as defined above, such as, for example, fatty acid ethyl esters or the esters resulting from transesterification of fatty acids with 2-ethylhexanol.

Standard EN 14214 (or Standard ASTM D6751) describes the requirements relating to FAMEs (FAMEs) used as biodiesel. One of the criteria is the cold filter plugging point (CFPP) according to the standard EN 116 in Europe (or according to Standard ASTM Method D 2500 in the USA). This CFPP criterion corresponds to the temperature of blockage of a cold filter in the presence of FAAE. This temperature depends in part on the content of residual saturated monoglycerides in the FAMEs resulting from transesterification. In particular, the content of residual monoglycerides in the FAMEs has to be less than or equal to 0.8% by weight with regard to the weight of the FAMEs, according to Standard EN 14214. This content of residual monoglycerides is measured according to Standard EN 14105 in biodiesels.

The document US2007/0151146 describes a process for the separation and then for the filtration, using adsorbent compounds (such as granular glucose, boric acid or diatomaceous earth), of the steryl glycosides from the biodiesel. This process can sometimes entrain a small portion of residual monoglycerides simultaneously with the steryl glycosides. On the other hand, the process described in this document does not make it possible to selectively, efficiently and simply extract virtually all the residual monoglycerides from FAMEs, in particular FAMEs highly charged with monoglycerides, that is to say comprising more than 2% by weight of monoglycerides.

An aim of the present invention is thus to provide a simple process for the selective extraction of residual monoglycerides from FAMEs, in order to improve the low-temperature behaviour of FAMEs and to render them usable as biodiesels (in accordance with Standard EN 14214).

A subject-matter of the present invention is thus a process for the selective extraction of monoglycerides present in a fraction of fatty acid alkyl esters (FAMEs), comprising at least one stage of liquid/liquid extraction by means:

of a polar solvent (PS) comprising a light alcohol, that is to say a lower aliphatic alcohol having a number of carbons within the range from 1 to 8, preferably from 1 to 5, indeed even better still from 1 to 4;

and optionally of a nonpolar solvent (NS) comprising a solvent which is immiscible with the light alcohol.

The term "liquid/liquid extraction" is understood to mean, within the meaning of the invention, an extraction during which the solvent(s) used is (are) liquid at the extraction temperature.

Advantageously, the light alcohol is chosen from methanol, ethanol, isopropanol, n-propanol, butanol, isobutanol, 2-ethylhexanol and their mixtures. According to a preferred embodiment of the invention, the light alcohol is methanol, which exhibits the advantage of already being used during the transesterification of the FAMEs. Advantageously, the process of selective extraction of monoglycerides according to the invention does not require the use of a special adsorbent product and does not require a subsequent filtration stage either.

The said polar solvent preferably comprises from 99.9 to 70% of light alcohol and from 0.1 to 30% of water, preferably from 80 to 99% of light alcohol and from 1 to 20% of water and preferably from 85 to 95% of light alcohol and from 5 to 15% of water. This is because the amount of monoglycerides extracted according to the process of the invention increases when the degree of hydration of the light alcohol increases (see the examples below).

Advantageously, the said nonpolar solvent is chosen from hexane, heptane, benzene, bicyclohexyl, cyclohexane, decalin, decane, hexane (Texsolve C), kerosene, methylcyclohexane, Texsolve S or S-66, naphtha (Texsolve V), Skellite, tetradecane, Texsolve (B, C, H, S, S-2, S-66, S-LO, V), supercritical $CO_2$, pressurized propane, pressurized butane, natural solvents, such as terpenes (limonene, α- and β-pinene, and the like) and their mixtures; and is preferably hexane. The use of a solvent which is immiscible with the light alcohol makes it possible to more easily separate the phase comprising the purified FAAEs from the phase comprising the monoglycerides extracted with the light alcohol.

The term "fraction of fatty acid alkyl esters (FAAEs)" is understood to mean, within the meaning of the invention, the combination formed by the fatty acid alkyl esters resulting from transesterification and their impurities which comprise in particular monoglycerides (also known as monoacylglycerols).

Preferably, the fraction of FAAEs comprises at least 90% by weight of fatty acid methyl esters (FAMES), with respect to the weight of the said fraction.

The fatty acid alkyl esters used as starting material in the process of the invention comprise at least one ester chosen, for example, from methyl esters of rapeseed, safflower, sunflower, nasturtium, mustard seed, olive, walnut, hazelnut, avocado, grape seed, sesame, soybean, maize, peanut, cottonseed, rice, babassu, castor, palm, palm kernel, lupin, jatropha, coconut, linseed, evening primrose, jojoba, camelina or algal oil, of tallow, such as beef or pork tallow, of fish, of chicken fat, of pig fat, of milk fatty matter, of shea butter, of biodiesel, of used cooking oil, of used frying oil, of miscella, of derivatives of these oils, in particular hydrogenated derivatives or conjugated derivatives, of the fractions of these oils, and their mixtures.

A fraction of fatty acid alkyl esters resulting from transesterification generally comprises from 0.5 to 5% by weight, more commonly from 0.8 to 3% by weight, of monoglycerides, with respect to the total weight of the said fraction, before the liquid/liquid extraction stage of the process of the invention.

According to the process of the invention, the monoglycerides are extracted into the phase comprising the light alcohol (phase of the polar solvent).

According to a preferred embodiment of the process of the invention, the polar solvent (PS) is introduced countercurrent-wise to the fraction of FAAEs, resulting in a heavy phase comprising the purified FAAEs being obtained and in a light phase enriched in monoglycerides being obtained.

This is because, when a nonpolar solvent, such as hexane, is not used, it is the phase comprising the light alcohol which has extracted the monoglycerides which is lighter than the phase comprising the purified FAAEs.

Preference is given to this embodiment, which uses only the polar solvent for the extraction (without nonpolar solvent) and which already exhibits an excellent extraction performance, as demonstrated in the examples below. Furthermore, the light alcohol, generally methanol is already available on site to carry out the transesterification. No attempt will thus be made to introduce, in addition and especially, a hydrocarbon which is not used up until then.

According to a second embodiment, the process of the invention comprises the following stages:

1—mixing the FAAEs with the NS and the PS, stirring the mixture obtained and then separating it by settling until a heavy phase 1 (HP1) enriched in monoglycerides is obtained and a light phase 1 (LP1) comprising the purified FAAEs is obtained.

In this second embodiment of the process of the invention, the nonpolar solvent is lighter than the polar solvent and it is the nonpolar solvent which comprises the purified ester.

According to an alternative form of this second embodiment, stage 1—is followed by the following stages in the process of the invention:

2—mixing, stirring and then separating by settling LP1+PS→HP2+LP2
3—mixing, stirring and then separating by settling HP1+HP2+NS→HP3+LP3
4—mixing, stirring and then separating by settling HP3+NS→HP4+LP4, in which:
HP4 is the heavy phase enriched in monoglycerides, and the sum of the light phases LP2+LP3+LP4 comprises the purified FAAEs, which preferably have a content of monoglycerides of less than or equal to 0.8% by weight, with regard to the weight of purified FAAEs.

The process according to the invention can be carried out without difficulty on the industrial scale, batchwise or continuously, using one or more devices chosen from mixers-settlers, mechanically stirred mixers, static mixers, gravity settlers, centrifugal decanters, coalescers, centrifugal liquid-liquid extractors, liquid-liquid hydrocyclones, extractors comprising separate stages, extractors comprising stages which are not separate (differential extractors), countercurrent columns, over one or more consecutive stages, in particular gravity columns, spray towers, packed columns, perforated plate columns, stirred columns, pulse columns or rotating disc columns, contacters and any other device used for liquid extraction. These liquid/liquid extraction devices are described in Parts J 2 764, J 2 765 and J 2 766 of the Techniques de l'Ingénieur [Technologies for the Engineer].

Advantageously, the process of the invention, whatever the embodiment described above, comprises at least two extraction stages. Advantageously, the said process comprises at least five extraction stages.

Preferably, the polar solvent/FAAEs ratio by weight is within the range from 1/5 to 5/1, preferably from 1/4 to 4/1 and preferably from 1/4 to 1/1.

Another subject-matter of the present invention is a fraction of fatty acid alkyl esters (FAAEs) of vegetable or animal origin capable of being obtained according to the process of the invention, characterized in that its content of monoglycerides is less than 0.6% by weight, preferably less than 0.5% by weight, preferably less than 0.4% by weight, preferably less than 0.3% by weight and preferably less than 0.25% by weight, with regard to the weight of the fraction of FAMEs.

A further subject-matter of the present invention is a biodiesel comprising a purified fraction of FAMEs having a content of monoglycerides of less than 0.6% by weight, preferably less than 0.5% by weight, preferably less than 0.4% by weight, preferably less than 0.3% by weight and preferably less than 0.25% by weight, with regard to the weight of the fraction of FAMEs; the said fraction being obtained according to the process of the invention.

A better understanding of the invention and its advantages will be obtained on reading the examples below, given purely by way of illustration and without implied limitation.

EXAMPLES

Unless otherwise indicated, all the percentages are given by weight.

The term "Φ" means "phase".

The following examples illustrate the liquid/liquid extraction processes according to the invention for the extraction of the monoglycerides (MGs) present in a fraction of fatty acid methyl esters (FAMEs) not in accordance with Standard EN 14214 as regards its content of residual monoglycerides (monoglycerides >0.8%).

For this, a complying rapeseed methyl ester (CRME) assaying, before doping, 0.4% of monoglycerides was deliberately doped with monoglycerides. Several doping levels were selected, in particular 1; 1.3 and 2.4%.

In examples 1 to 3, liquid-liquid extraction tests were carried out in the presence of a mixture of polar (PS) and nonpolar (NS) solvents, in this case hydrated methanol and hexane, in Examples 1 and 2, according to the following procedure:

1. 5 g of MG-doped CRME+30 ml NS+15 ml PS→heavy Φ1+light Φ1
2. Light Φ1+15 ml PS→heavy Φ2+light Φ2
3. Heavy Φ1+heavy Φ2+30 ml NS→heavy Φ3+light Φ3
4. Heavy Φ3+30 ml NS→heavy Φ4+light Φ4

NS: nonpolar solvent (hexane)
PS: polar solvent (methanol/water at different water contents).

Concentration:
1. Heavy Φ4→polar fraction
2. Light Φ2+light Φ3+light Φ4→nonpolar fraction In examples 1 to 4, the solvent is removed for each fraction or final phase by vacuum distillation on a rotary evaporator, at 90° C. and under a vacuum of 20 mbar. Thus, in the following Tables 1 to 9, the "distributions by weight" are given as %, after evaporation of the solvent. Likewise, the contents of monoglycerides (%) are measured with respect to the "dry weight" (once the solvent has been evaporated) of the phase which comprises the purified FAMEs.

Example 1

The analytical balance of the purified esters starting from a fraction of methyl esters highly charged with monoglycerides (2.4%) is described in detail in the following Table 1.

TABLE 1

|  | Test No. 5 | Test No. 1 | Test No. 2 |
|---|---|---|---|
| Polar solvent (% methanol/% water) | 80/20 | 90/10 | 99/1 |
| Nonpolar solvent | Hexane | Hexane | Hexane |
| Heavy polar phase (methanol-rich) distribution by weight, % after evaporation of the solvents | 0.8 | 1.5 | 3.7 |
| Light nonpolar phase (hexane-rich) distribution by weight, % after evaporation of the solvents | 99.2 | 98.5 | 96.3 |
| MonoGlyceride content (%), starting material, % | 2.4 | 2.4 | 2.4 |
| MonoGlyceride content (%), light phase, % | 1.63 | 0.95 | 1.16 |
| MonoGlyceride extraction yield, light phase, % | 32.0 | 60.7 | 53.1 |

Comments:

The amount of material extracted into the light phase decreases when the degree of hydration of the methanol tends to fall.

For all that, the extraction selectivity for the monoglycerides passes through a maximum as a function of the water content of the polar solvent, for a methanol/water ratio by weight within the range from 80/20 to 99/1.

The process according to the invention makes it possible to reduce by a factor of 2.5 the monoglyceride content of a fraction of methyl esters initially highly charged.

Example 2

The analytical balance of the purified esters starting from a fraction of methyl esters moderately charged (1.3%) with monoglycerides is described in detail in the following Table 2.

TABLE 2

|  | Test No. 6 | Test No. 3 | Test No. 4 |
|---|---|---|---|
| Polar solvent (% methanol/% water) | 80/20 | 90/10 | 99/1 |
| Nonpolar solvent | Hexane | Hexane | Hexane |
| Heavy polar phase distribution by weight, % after evaporation of the solvents | 0.7 | 1.4 | 3.0 |
| Light nonpolar phase distribution by weight, % after evaporation of the solvents | 99.3 | 98.6 | 97.0 |
| MonoGlyceride content (%), starting material, % | 1.3 | 1.3 | 1.3 |
| MonoGlyceride content (%), light phase, % | 1.00 | 0.65 | 0.79 |
| MonoGlyceride extraction yield, light phase, % | 25.9 | 52.2 | 42.8 |

Comments:

The amount of material extracted into the light phase decreases when the degree of hydration of the methanol tends to fall.

For all that, the extraction selectivity for the monoglycerides passes through a maximum as a function of the water content of the polar solvent, for a methanol/water ratio within the range from 80/20 to 99/1.

The process according to the invention makes it possible to reduce by a factor of 2 the monoglyceride content of a highly charged methyl ester. Thus, a methyl ester not in accordance with the European standard for biodiesel (monoglyceride >0.8%) can be purified by liquid-liquid extraction.

Example 3

The analytical balance of the purified esters starting from a fraction of FAMEs moderately charged with monoglycerides (1.03%) is described in Table 3 below.

TABLE 3

|  | Test No. 7 |
|---|---|
| Polar solvent (% methanol/% water) | 90/10 |
| Nonpolar solvent | Hexane |
| Heavy polar phase distribution by weight, % | 0.8 |
| Light nonpolar phase distribution by weight, % | 99.2 |
| MonoGlyceride content (%), starting material, % | 1.03 |
| MonoGlyceride content (%), light phase, % | 0.35 |
| MonoGlyceride extraction yield, light phase, % | 66.2 |

Comments:

the selectivity of the process is confirmed since an extraction yield for the monoglycerides of 66% is obtained starting from a batch of ester moderately charged with monoglycerides. The FAME resulting from the light phase is then in accordance with the European standard for biodiesel (monoglyceride content <0.8%).

Example 4

Purification Tests on a Countercurrent Column a) Extraction by a polar solvent, according to a single-stage extraction, of the MGs from a fraction of FAMEs which is moderately charged:

Procedure: 20 g MG-doped CRME+20 g PS→heavy Φ1+light Φ1

| Test No. 8 | Crude weight, g | Dry weight, g |
|---|---|---|
| Heavy Φ 1 | 21.0 | 19.2 |
| Light Φ 1 | 19.0 (methanol-rich) | 0.8 (after evaporation of the solvent) |

The analytical balance of the purified esters starting from a fraction of FAMEs moderately charged with MG (1.03%) is given in Table 4 below:

TABLE 4

|  | Test No. 8 |
| --- | --- |
| Polar solvent (% methanol/% water) | 90/10 |
| Nonpolar solvent | None |
| Heavy phase distribution by weight, % | 96.0% |
| Light phase (methanol-rich) distribution by weight, % after evaporation of the solvent | 4.0% |
| MonoGlyceride content (%), starting material, % | 1.0 |
| MonoGlyceride content (%), heavy phase, % | 0.64 |
| MonoGlyceride extraction yield, % | 40.3 |

Comments:

In the absence of hexane, entrainment of the monoglycerides by the methanol occurs. The methanol becomes the light phase.

In a single extraction and in the presence solely of hydrated methanol (10/90), the MGs are extracted with a yield of 40%, making it possible to bring the MG content back to conforming levels (biodiesel), this being achieved with a high yield of purified FAME (96%). This test demonstrates the feasibility of the process with a solvent/ester ratio which is realistic industrially.

The methanol-rich phase, comprising the monoglycerides but also methyl esters, can be easily recycled upstream of the extraction process in the transesterification unit, where the process for the conversion of the monoglycerides will be repeated until complete conversion is achieved, so that there is no loss of material.

b) Single-stage extraction by a polar solvent of the MGs from a fraction of esters which is weakly charged:

Procedure: 20 g CRME+20 g PS→heavy Φ1+light Φ1

| Test No. 9 | Crude weight, g | Dry weight, g |
| --- | --- | --- |
| Heavy Φ 1 | 21.0 | 19.2 |
| Light Φ 1 | 19.0 | 0.8 |

The analytical balance of the purified esters starting from a batch of esters which is weakly charged (0.67% of MGs) is given in Table 5 below.

TABLE 5

|  | Test No. 9 |
| --- | --- |
| Polar solvent (% methanol/% water) | 90/10 |
| Solvent/CRME ratio | 1/1 |
| Light phase distribution by weight, % | 4.0% |
| Heavy phase distribution by weight, % | 96.0% |
| MonoGlyceride content (%), starting material, % | 0.67 |
| MonoGlyceride content (%), heavy phase, % | 0.34 |
| MonoGlyceride extraction yield, % | 51.3 |

Comments:

The MGs are extracted with a yield of the order of 50%, making it possible to bring the MG content back to very low levels (<0.4%), this being achieved with a high yield of purified ester (96%). This test demonstrates the feasibility of the process with a solvent/ester ratio which is realistic industrially.

c) Two-stage extraction of the MGs by a polar solvent

Procedure:

20 g currently conforming CRME+20 g PS→heavy Φ1+light Φ1

Heavy Φ1+20 g PS→heavy Φ2+light Φ2

| Test No. 10 | Crude weight, g | Dry weight, g |
| --- | --- | --- |
| Heavy Φ 1 | 20.9 | 19.2 |
| Light Φ 1 (methanol-rich) | 19.1 | 0.8 |
| Light Φ 2 (methanol-rich) | 20.6 | 0.9 |
| Heavy Φ 2 | 20.3 | 18.3 |

The analytical balance of the purified esters starting from a batch of esters which is weakly charged (0.67% of MGs) by countercurrent two-stage extraction is shown in Table 6.

TABLE 6

|  | Test No. 10 |
| --- | --- |
| Polar solvent (% methanol/% water) | 90/10 |
| Solvent/CRME ratio | 1/1 |
| Light phase 1 distribution by weight, % | 4.0 |
| Light phase 2 distribution by weight, % | 4.3 |
| Heavy phase 2 distribution by weight, % | 91.7 |
| MonoGlyceride content (%), starting material, % | 0.67 |
| MonoGlyceride content (%), heavy phase, % | 0.21 |
| MonoGlyceride extraction yield, % | 71.3 |

Comments:

Starting from an ester weakly charged with MGs, the extraction of the glycerides is efficiently carried out countercurrent-wise over two stages: MG extraction yield >71% and MG content of the purified esters of 0.2% approximately. The purified ester yield of the process is greater than 90%, it being possible for the fraction enriched in MGs to be recycled in the transesterification. This test confirms the industrial relevance of the process according to the invention.

d) Single-stage extraction of the MGs by a polar solvent—Influence of the polar solvent/FAME ratio:

The objective is to evaluate the influence of the polar solvent/ester ratio with the aim of reducing the amounts of solvent involved. A solvent/ester ratio of 1/2 was tested.

Procedure: 20 g CRME+10 g PS→heavy Φ1+light Φ1

| Test No. 11 | Crude weight, g | Dry weight, g |
| --- | --- | --- |
| Heavy Φ 1 | 21.2 | 19.5 |
| Light Φ 1 | 8.8 | 0.5 |

The analytical balance of the purified esters starting from a batch of esters which is weakly charged (0.67% of MGs) is shown in Table 7 below, which esters were purified by countercurrent single-stage extraction with a solvent/ester ratio of 1/2.

TABLE 7

|  | Test No. 11 |
| --- | --- |
| Polar solvent (% methanol/% water) | 90/10 |
| Solvent/CRME ratio | 1/2 |
| Light phase distribution by weight, % | 2.4% |
| Heavy phase distribution by weight, % | 97.6% |
| MonoGlyceride content (%), starting material, % | 0.67 |

TABLE 7-continued

|  | Test No. 11 |
| --- | --- |
| MonoGlyceride content (%), heavy phase, % | 0.41 |
| MonoGlyceride extraction yield, % | 40.3 |

Comments:

In comparison with Test 9, a reduction by half in the amount of solvent involved makes it possible to maintain a high MG extraction yield of 40% and to achieve a residual MG content in the purified esters of approximately 0.4%, very slightly greater than Test 9 (0.34%) but far below the current specifications for biodiesel. The overall yield of purified ester is logically improved: 97.6% vs 96.0% in Test 9.

e) Two-stage extraction of the MGs by a polar solvent on a two-stage column—Influence of the solvent/ester ratio Procedure:

20 g currently conforming CRME+10 g PS→heavy Φ1+light Φ1

Heavy Φ1+10 g PS→heavy Φ2+light Φ2

| Test No. 12 | Crude weight, g | Dry weight, g |
| --- | --- | --- |
| Heavy Φ 1 | 21.1 | 19.7 |
| Light Φ 1 (MeOH) | 8.9 | 0.3 |
| Light Φ 2 (MeOH) | 10.1 | 0.5 |
| Heavy Φ 2 | 21.0 | 19.2 |

The analytical balance of the purified esters starting from a batch of esters which is weakly charged (0.67% of MGs), countercurrent two-stage extraction with a solvent/ester ratio of 1/2, is shown in Table 8.

TABLE 8

|  | Test No. 12 |
| --- | --- |
| Polar solvent (% methanol/% water) | 90/10 |
| Solvent/CRME ratio | 1/2 |
| Light phase 1 distribution by weight, % | 1.5% |
| Light phase 2 distribution by weight, % | 2.5% |
| Heavy nonpolar phase 2 distribution by weight, % | 96.0% |
| MonoGlyceride content (%), starting material, % | 0.67 |
| MonoGlyceride content (%), heavy phase, % | 0.32 |
| MonoGlyceride extraction yield, % | 54.1 |

Comments:

In comparison with Test 10, a reduction by half in the amount of solvent involved makes it possible to maintain a high extraction yield of 54% and to achieve a residual monoglyceride content in the purified esters of 0.3% approximately, very slightly greater than Test (0.2%) but far below the current specifications for biodiesel. The overall yield of purified ester is logically improved: 96.0% vs 91.7% in Test 10.

Example 5

Multistage (Five-Stage) Countercurrent Extraction by a Polar Solvent of the Monoglycerides from a Methyl Ester Procedure for Simulation of an Extraction on a Countercurrent (Five-Stage) Column:

40 g currently conforming (0.67%) CRME+10 g PS→heavy Φ1+light Φ1

The polar solvent/FAME ratio by weight is equal to 1/4. Five separating funnels are installed and are named A1, A2, A3, A4 and A5.

1. The five funnels are charged with 40 g of ester and 10 g of hydrated methanol 10/90, are agitated well and left to separate by settling. H1 is the upper phase of funnel No. 1 and B1 is the lower phase of funnel No. 1, and so on for the other funnels.
2. B1 is withdrawn into a round-bottomed flask and concentrated, H1 is placed in a beaker and 10 g of methanol are placed in funnel No. 1.
3. B2 is placed in funnel No. 1, H2 is placed in a beaker and H1 is placed in funnel No 2.
4. B3 is placed in funnel No. 2, H3 is placed in a beaker and H2 is placed in funnel No. 3.
5. B4 is placed in funnel No. 3, H4 is placed in a beaker and H3 is placed in funnel No. 4.
6. B5 is placed in funnel No. 4, H5 is placed in a round-bottomed flask and concentrated, and H4 and 40 g of methyl ester are placed in funnel No. 5. All the funnels are subsequently agitated and then left to separate by settling.

Stages 2 to 6 form a first sequence representing the 1st extraction stage. Phases B1 and H5 are then weighed and analysed (see Table 9, end sequence 1). The continuation of the test consists in starting the second sequence in the presence of the contents of the funnels resulting from the preceding sequence and in reinjecting fresh methanol and starting material ester, respectively, into funnels 1 and 5. And so on, until five complete sequences have been carried out. In fact, the five sequences simulate the operation of the five-stage column. The mass and analytical balances carried out on the phases exiting at the end of each sequence are represented in Table 9.

BRIEF DESCRIPTION OF THE DRAWING

FIG. 1 gives a diagrammatic representation of the extraction on a countercurrent (five-stage) column.

The mass and analytical balance of the countercurrent extraction over five stages is shown in Table 9 (the DW percentages are given for the dry weight).

TABLE 9

|  | % light phase (which was rich in MeOH) (% DW) | % heavy phase (% DW) | Monoglyceride content, heavy phase (% DW) | Monoglyceride extraction yield (%) |
| --- | --- | --- | --- | --- |
| Starting material | — | 100 | 0.67 | — |
| End sequence 1 | 0.7 | 99.3 | 0.49 | 27.3 |
| End sequence 2 | 0.4 | 99.6 | 0.45 | 33.1 |
| End sequence 3 | 0.4 | 99.6 | 0.45 | 33.1 |
| End sequence 4 | 0.8 | 99.2 | 0.45 | 33.4 |
| End sequence 5 | 0.5 | 99.5 | 0.44 | 34.7 |

Comments:

after a 1st extraction stage, the MG content rapidly decreases (below 0.5%);

the MG content rapidly reaches a plateau of 0.45% from the second sequence since it barely changes subsequently during the extraction;

the overall yield of esters subsequent to the five extraction stages is 97.2% and the overall MG extraction yield is 34.6%.

The results of the tests of Examples 1 to 5 according to the invention demonstrate the effectiveness of the liquid-liquid extraction process in the presence of hydrated methanol as extraction solvent.

The invention claimed is:

1. A process for the selective extraction of monoglycerides present in a fraction of fatty acid alkyl esters (FAAEs), comprising at least one selective liquid/liquid extraction of monoglycerides from PAAEs by:
   a polar solvent (PS) comprising a light alcohol,
   and of a nonpolar solvent (NS) comprising a solvent which is immiscible with the light alcohol.

2. The process according to claim 1, in which the light alcohol is methanol, ethanol, isopropanol, n-propanol, butanol, isobutanol, 2-ethylhexanol or their mixtures.

3. The process according to claim 1, in which the polar solvent comprises from 99.9 to 70% of light alcohol and from 0.1 to 30% of water.

4. The process according to claim 1, in which the nonpolar solvent is hexane, heptane, benzene, bicyclohexyl, cyclohexane, decalin, decane, hexane, kerosene, methylcyclohexane, Texsolve S or S-66, naphtha, Skellite, tetradecane, Texsolve, supercritical $CO_2$, pressurized propane, pressurized butane, natural solvents or their mixtures.

5. The process according to claim 1, in which the FAAEs comprise at least one ester of rapeseed, safflower, sunflower, nasturtium, mustard seed, olive, sesame, soybean, maize, peanut, walnut, hazelnut, avocado, grape seed, cottonseed, rice, babassu, castor, palm, palm kernel, lupin, jatropha, coconut, linseed, evening primrose, jojoba, camelina or algal oil, of tallow, beef or pork tallow, of chicken fat, of pig fat, of fish, of milk fatty matter, of shea butter, of biodiesel, of used cooking oil, of used frying oil, of miscella, of hydrogenated derivatives or conjugated derivatives of the fractions of these oils, or their mixtures.

6. The process according to claim 1, in which the fraction of FAAEs is from 0.5 to 5% by weight of monoglycerides with regard to the total weight of the fraction of esters before the liquid/liquid extraction stage.

7. The process according to claim 1, in which the fraction of FAAEs is at least 90% by weight of fatty acid methyl esters (FAMEs), with respect to the weight of the fraction.

8. The process according to claim 1, in which the light alcohol is methanol.

9. The process according to claim 1, in which the nonpolar solvent is hexane.

10. The process according to claim 1, in which the polar solvent (PS) is introduced countercurrent-wise to the fraction of FAAEs, resulting in a heavy phase comprising the purified FAAEs and in a light phase enriched in monoglycerides.

11. The process according to claim 1, comprising: mixing the FAAEs with the NS and the PS, stirring the mixture obtained and then separating it by settling, resulting in a heavy phase (HP1) enriched in monoglycerides and a light phase (LP1) comprising the purified FAAEs.

12. The process according to claim 1, comprising at least two extraction stages.

13. The process according to claim 12, comprising at least five extraction stages.

14. The process according to claim 1, in which the polar solvent/FAAEs ratio by weight is within the range from 1/5 to 5/1.

15. A fraction of fatty acid alkyl esters (FAAEs) of vegetable or animal origin capable of being obtained according to the process of claim 1, having a content of monoglycerides less than 0.4% by weight with regard to the weight of the fraction of FAAEs.

16. Biodiesel comprising a purified fraction of FAAEs having a content of monoglycerides of less than 0.4%, the said fraction being obtained according to the process of claim 1.

17. The process according to claim 1, wherein the tallow is beef or pork tallow.

18. The process according to claim 1, in which the polar solvent/FAAEs ratio by weight is within the range from 1/4 to 4/1.

19. The process according to claim 1, in which the polar solvent/FAAEs ratio by weight is within the range from 1/4 to 1/1.

20. A fraction of fatty acid alkyl esters (FAAEs) of vegetable or animal origin capable of being obtained according to the process of claim 1, having a content of monoglycerides less than 0.3% by weight with regard to the weight of the fraction of FAAEs.

21. A fraction of fatty acid alkyl esters (FAAEs) of vegetable or animal origin capable of being obtained according to the process of claim 1, having a content of monoglycerides less than 0.25% by weight with regard to the weight of the fraction of FAAEs.

* * * * *